United States Patent
Walsdorff et al.

(12)

(10) Patent No.: US 6,916,953 B2
(45) Date of Patent: Jul. 12, 2005

(54) INTEGRATED PROCESS FOR PREPARING ISOCYANATES

(75) Inventors: Christian Walsdorff, Ludwigshafen (DE); Martin Fiene, Niederkirchen (DE); Eckhard Ströfer, Mannheim (DE); Klaus Harth, Altleiningen (DE); Jan D. Jacobs, Baton Rouge, LA (US); Filip Deberdt, Muinzen (BE)

(73) Assignee: BASF Aktiengesellschaft, Ludwigshafen (DE)

( * ) Notice: Subject to any disclaimer, the term of this patent is extended or adjusted under 35 U.S.C. 154(b) by 228 days.

(21) Appl. No.: 10/227,865

(22) Filed: Aug. 27, 2002

(65) Prior Publication Data

US 2004/0024244 A1 Feb. 5, 2004

(30) Foreign Application Priority Data

Aug. 2, 2002 (DE) ......................................... 102 35 476

(51) Int. Cl.$^7$ ..................... C07C 263/10; C07C 263/00; C07C 263/18; C07C 263/20
(52) U.S. Cl. ..................... 560/341; 560/330; 560/336; 560/338; 205/436; 205/438; 205/455; 205/456; 205/551
(58) Field of Search ................................ 205/551, 436, 205/438, 456, 455; 560/330, 336, 338, 341

(56) References Cited

U.S. PATENT DOCUMENTS

| 3,084,028 A | 4/1963 | Foulletier et al. |
|---|---|---|
| 3,660,261 A | 5/1972 | Wright et al. |
| 6,010,612 A * | 1/2000 | Freire et al. ................. 205/551 |

FOREIGN PATENT DOCUMENTS

| DE | 1 255 643 | 12/1967 |
|---|---|---|
| DE | 1 800 844 | 6/1970 |
| DE | 197 26 530 | 12/1998 |
| EP | 0 876 335 | 11/1998 |
| JP | 2000-75319 | 3/2000 |
| WO | WO 01/00569 | 1/2001 |
| WO | WO 01/00569 * | 1/2004 |

OTHER PUBLICATIONS

Derwent Abstracts, DE 199 28 741, Dec. 28, 2002.
Ullman's Enc. of Lud. Chem, 5$^{TH}$ Ed., vol. A6, pp. 463–466.

* cited by examiner

*Primary Examiner*—Elvis O. Price
(74) *Attorney, Agent, or Firm*—Oblon, Spivak, McClelland, Maier & Neustadt, P.C.

(57) ABSTRACT

Process for preparing organic isocyanates, which comprises the steps
(a) making available a first partial amount of chlorine, with the chlorine of this first partial amount having a content of free and bound bromine and iodine of <400 ppm;
(b) making available a second partial amount of chlorine;
(c) reacting the first and second partial amounts of chlorine with carbon monoxide to form phosgene;
(d) reacting the phosgene from step (c) with one or more primary amines to form the corresponding isocyanates and hydrogen chloride;
(e) separating off and, if necessary, purifying the isocyanates formed in step (d);
(f) separating off and, if necessary, purifying the hydrogen chloride formed in step (d);
(g) catalytically oxidizing at least part of the hydrogen chloride separated off in step (e) by means of oxygen to form chlorine;
(h) separating off the chlorine formed in step (g) and using at least a partial amount of the chlorine which has been separated off as second partial amount of chlorine in step (b).

10 Claims, 1 Drawing Sheet

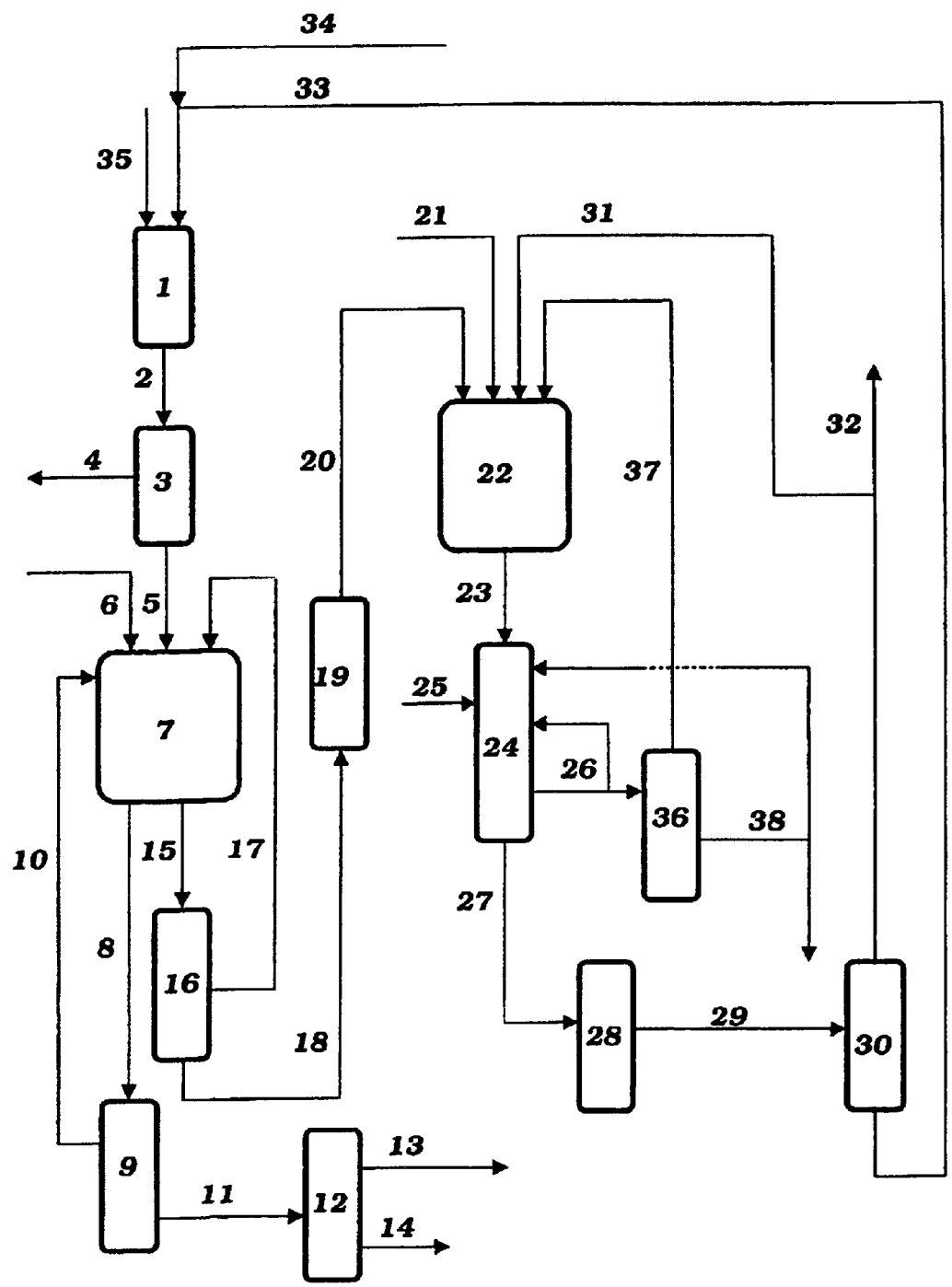

INTEGRATED PROCESS FOR PREPARING ISOCYANATES

The invention relates to a process for preparing isocyanates.

Isocyanates and isocyanate mixtures are prepared by known methods by phosgenation of the corresponding amines. For polyurethane foams, for example, bifunctional or polyfunctional aromatic isocyanates of the diphenylmethane diisocyanate series (MDI) are employed. Due to the production process, dark-colored products are often obtained after the phosgenation and the subsequent work-up (removal of the solvent; removal of monomeric MDI) and these in turn give yellowish polyurethane foams or other, likewise discolored, polyurethane materials. This is undesirable, since such coloration detracts from the overall visual impact and allows slight inhomogeneities to occur, e.g. as streaks in the foams obtained. Light-colored isocyanates or isocyanates which contain a reduced amount of color-imparting components are therefore preferred as raw materials.

Furthermore, the presence of bromine and of iodine reduces the yield due to by-product formation. The removal of the by-products increases the outlay required for separation tasks. In addition, product of value is lost during the removal of the by-products.

WO 01/00569 discloses a process for preparing isocyanates which contain only small amounts, if any, of color-imparting components, which leads, without further pretreatment or after-treatment steps, to light-colored isocyanates which are suitable for producing polyurethanes having no color or only a slight color. In this process, phosgene containing less than 50 ppm of bromine or bromine-containing compounds or iodine or iodine-containing compounds is used in the preparation of the isocyanates.

Chlorine is produced industrially from rock salt, sea salt or mined potassium chloride. Here, chlorine is usually produced together with sodium or sodium hydroxide as coproduct by electrolysis of a rock salt solution. Potassium chloride is used analogously for the production of chlorine together with potassium or potassium hydroxide. The salts used in the electrolysis usually contain bromine and iodine compounds in amounts of from 30 to 3000 ppm and these form bromine or iodine during the electrolysis.

A disadvantage of the above-described process is the high cost of purification required to reduce the bromine and iodine content in the chlorine used for the phosgene synthesis to such an extent that the resulting phosgene to be used in isocyanate production has the necessary low content of bromine, iodine, bromine-containing or iodine-containing compounds.

EP-A 0 876 335 discloses a process for preparing isocyanates from phosgene and amines, in which the hydrogen chloride obtained in isocyanate production is oxidized electrolytically to produce chlorine. The chlorine obtained is recycled to the phosgene synthesis. However, the electrolysis of hydrogen chloride is associated with high electricity costs. In addition, hydrogen is formed as coproduct in this process, which can cause safety problems. In the abovementioned document, it is stated that the electrolytically produced hydrogen is used for the production of amines from the corresponding nitro compounds. However, this advantage disappears if the isocyanate production is not back-integrated to the preparation of the amines from the corresponding nitro compounds. In any case, the hydrogen formed in the electrolysis of hydrogen chloride is not sufficient for the reduction of the nitro compounds. A further disadvantage is that even slight traces of organic compounds, for example solvent residues from isocyanate production, interfere in the sensitive hydrogen chloride electrolysis, so that the hydrogen chloride used has to be very pure.

It is an object of the present invention to provide an efficient process for preparing light-colored isocyanates, which makes do without further pretreatment or after-treatment steps for lightening the color of the isocyanates obtained and in which the need for purification of the raw materials used is minimal.

We have found that this object is achieved by a process for preparing light-colored organic isocyanates, which comprises the steps
(a) making available a first partial amount of chlorine, with the chlorine of this first partial amount having a content of free and bound bromine and iodine of <400 ppm;
(b) making available a second partial amount of chlorine;
(c) reacting the first and second partial amounts of chlorine with carbon monoxide to form phosgene;
(d) reacting the phosgene from step (c) with one or more primary amines to form the corresponding isocyanates and hydrogen chloride;
(e) separating off and, if necessary, purifying the isocyanates formed in step (d);
(f) separating off and, if necessary, purifying the hydrogen chloride formed in step (d);
(g) catalytically oxidizing at least part of the hydrogen chloride separated off in step (e) by means of oxygen to form chlorine;
(h) separating off the chlorine formed in step (g) and using at least a partial amount of the chlorine which has been separated off as second partial amount of chlorine in step (b).

In a step (a), a first partial amount of chlorine is made available. The chlorine of the first partial amount has a content of free and bound bromine and iodine of <400 ppm. Here, 1 ppm of bromine or iodine means 1 atom of bromine or iodine per 1 000 000 halogen atoms. The upper limit of 400 ppm relates to the sum of the two elements.

Bromine and iodine can be present in the chlorine in molecular (free) form as $Br_2$ or $I_2$ or also in bound form, for example as BrCl and ICl.

Processes for preparing appropriate chlorine having a low content of bromine and iodine are known to those skilled in the art. In principle, it is possible to use any chlorine which meets the abovementioned specification, i.e. less than about 400 ppm of bromine and iodine, for the purposes of the present invention. Thus, for example, it is possible to use chlorine which has been produced by electrolysis processes or by oxidation of hydrogen chloride, e.g. by the Deacon process, as long as the hydrogen chloride used also has a sufficiently low bromine and iodine content.

In one embodiment of the invention, the chlorine of the first partial amount is produced by electrolysis of a solution containing chloride ions. In general, this is an aqueous rock salt solution, an aqueous potassium chloride solution or aqueous hydrogen chloride (hydrochloric acid).

Thus, the chlorine synthesis can be carried out using appropriate starting materials which themselves have a low bromine and iodine content, e.g. low-bromine and low-iodine salts or low-bromine and low-iodine hydrochloric acid. Such low-bromine and low-iodine salts having a total bromine and iodine content of <400 ppm are mined, for example, at Heilbronn, Germany.

The preparation of chlorine having a particularly low bromine content can also be carried out, as described in U.S.

Pat. No. 3,660,261, by oxidative treatment of the salt used for the electrolysis.

In a further embodiment of the invention, the chlorine of the first partial amount is subjected after its production to a purification step in which its bromine and/or iodine content is reduced.

One possible way of reducing the amount of bromine in bromine-containing chlorine is described in Ullmann's Encyclopedia of Industrial Chemistry, 5th edition, volume A6, p. 463 and FIG. 70 on p. 465: when gaseous bromine-rich chlorine is scrubbed in countercurrent with liquid low-bromine chlorine, the chlorine gas to be purified is depleted in bromine and the liquid chlorine is enriched with bromine. For the start-up of such a plant, it is necessary for a sufficient amount of low-bromine liquid chlorine to be made available at the beginning, after which a substream of the relatively low-bromine chlorine obtained can be liquefied and used for scrubbing the relatively bromine-rich chlorine. This process is carried out in columns provided with customary separation-active internals such as trays, random packing or ordered packing. The degree of depletion in bromine or iodine achieved depends in the manner customary for absorption and distillation processes on the system pressure, the flows, the concentrations and on the internals used. The design of the column on the basis of the desired degree of depletion in bromine is therefore a purely routine task.

An alternative is to remove bromine or iodine from chlorine by means of distillation, selective condensation of the bromine or iodine in the chlorine stream or by reactions with substances which react selectively with bromine and/or iodine, as described, for example, in JP 0075319. Suitable processes are also described in DE-A 18 00 844, DE-B 12 55 643 or in DE-A1 197 26 530.

The chlorine used as first partial amount preferably contains less than 200 ppm of bromine and iodine, particularly preferably less than 50 ppm of bromine and iodine.

In a step (b), a second partial amount of chlorine is made available. At the commencement of operation of the process of the present invention, i.e. during the "start-up phase", and also when the production amount is altered during operation of the process or during the "running-down phase", the chlorine of the second partial amount can have the same content or even a significantly higher content of bromine and iodine, but it preferably has the same content or a lower content of bromine and iodine. In particular, the chlorine of the first and second partial amounts during the start-up phase come from the same source. When operation of the process of the present invention has gone beyond the start-up phase and a sufficient amount of chlorine is available from the separation step (h) as second partial amount, this partial amount will in any case have a significantly lower bromine and iodine content than the chlorine of the first partial amount, since the chlorine recovered in step (h) has already gone through the steps of phosgene synthesis (c) and isocyanate production (d). The bromine and iodine present in the chlorine used or in the phosgene prepared therefrom reacts with the amines and isocyanates during isocyanate production (d) to give compounds brominated or iodinated in the ring and side chains and thus remain bound in these compounds. In this way, bromine or iodine is "scrubbed" from the chlorine used. A steady state in which the chlorine recovered in step (h) and used as second partial amount has a very much lower bromine and iodine content than the chlorine of the first partial amount or is even virtually free of bromine or iodine is established, so that the chlorine used in step (c) has overall a very much lower bromine or iodine content than the chlorine of the first partial amount introduced into the process. Thus, only the isocyanate obtained during the start-up phase of the process of the present invention is "contaminated" with relatively high bromine and iodine contents, while the isocyanate prepared in a later phase has only come into contact with the very much lower steady-state bromine and iodine contents. The initial contamination can be reduced by using particularly pure chlorine as chlorine of the first partial amount during the start-up phase.

Under steady-state conditions, it is preferred that essentially the total amount of the chlorine separated off in step (h) is used as second partial amount of chlorine in step (b), and the first partial amount of chlorine is calculated so that the sum of the first and second partial amounts remains constant. In other words, the first partial amount merely compensates for losses in chlorine occurring in the steps (c) to (h).

The second partial amount of chlorine usually makes up at least 70% of the sum of the first and second partial amounts of chlorine.

If the proportion of the (recirculated) second partial amount of chlorine is, for example, about 80% of the sum of the first and second partial amounts of chlorine, the amount of bromine and iodine introduced at a given bromine and iodine content in the chlorine used is only about ⅕ of the amount which would be introduced without chlorine recycling. Thus, even comparatively high bromine or iodine contents can be tolerated in the first partial amount of chlorine while still obtaining light-colored isocyanates without further pretreatment or after-treatment steps. The outlay associated with reducing the amounts of bromine and iodine in the chlorine used may be eliminated entirely. On the other hand, use of low-bromine and low-iodine chlorine in the process of the present invention makes it possible to achieve very much higher purities of the isocyanate prepared than would otherwise be the case.

In a step (c), the first and second partial amounts of chlorine are reacted with carbon monoxide to form phosgene. Methods of preparing phosgene are described in Ullmanns Enzyklopädie der industriellen Chemie, 3rd edition, vol. 13, pages 494–500. Thus, phosgene can be obtained by passing carbon monoxide and chlorine over activated carbon.

In a step (d), phosgene is reacted with one or more amines to give the corresponding isocyanates and hydrogen chloride. This reaction is also referred to as phosgenation of the amines. The amines used have at least one primary amino group, preferably two primary amino groups and possibly also three or more primary amino groups.

The preparation of isocyanate taking place in the process of the present invention is carried out in a manner known to those skilled in the art by reacting an amine or a mixture of two or more amines with a superstoichiometric amount of phosgene. It is in principle possible to employ all processes in which a primary amine or a mixture of two or more primary amines having one or more primary amino groups with phosgene to form one or more isocyanates having one or more isocyanate groups.

In a preferred embodiment of the invention, the phosgenation of the amine or amines is carried out in a solvent or solvent mixture. As solvent, it is possible to use all solvents suitable for the preparation of isocyanates. These are preferably inert aromatic, aliphatic or alicyclic hydrocarbons or their halogenated derivatives. Examples of such solvents are aromatic compounds such as monochlorobenzene or dichlorobenzene, for example o-dichlorobenzene, toluene, xylenes, naphthalene derivatives such as tetralin or decalin, alkanes having from about 5 to about 12 carbon atoms, e.g. hexane, heptane, octane, nonane or decane, cycloalkanes such as cyclohexane, effectively inert esters and ethers such as ethyl acetate or butyl acetate, tetrahydrofuran, dioxane or diphenyl ether. It is also possible to recirculate a substream of the isocyanate produced as solvent or solvent constituent.

Suitable amines are in principle all primary amines which can react in an appropriate manner with phosgene to form isocyanates. Linear or branched, saturated or unsaturated aliphatic or cycloaliphatic or aromatic primary monoamines or polyamines which can be reacted with phosgene to give isocyanates are all suitable in principle. Examples of useful amines are 1,3-propylenediamine, 1,4-butylenediamine, 1,5-pentamethylenediamine, 1,6-hexamethylenediamine and the corresponding higher homologues in the series, isophoronediamine (IPDA), cyclohexylenediamine, cyclohexylamine, aniline, phenylenediamine, p-toluidine, 1,5-naphthylenediamine, 2,4- or 2,6-toluenediamine or mixtures thereof, 4,4'-, 2,4'- or 2,2'-diphenylmethanediamine or mixtures thereof, and also higher molecular weight isomeric, oligomeric or polymeric derivatives of the abovementioned amines and polyamines.

In a preferred embodiment of the present invention, the amines used are the isomeric primary diphenylmethanediamines (MDA) or their oligomeric or polymeric derivatives, i.e. the amines of the diphenylmethanediamine series. Diphenylmethanediamine, its oligomers or polymers are obtained, for example, by condensation of aniline with formaldehyde. Such oligoamines or polyamines or their mixtures are also used in a preferred embodiment of the invention. Further preferred amines are hexamethylenediamine, toluenediamine and isophoronediamine.

The reaction (d) of the low-bromine and low-iodine phosgene with the abovementioned amines can be carried out continuously or batchwise in one or more stages. If a single-stage reaction is carried out, this is preferably carried out at from about 40 to 200° C., for example at from about 90 to 180° C.

In a preferred embodiment of the invention, the reaction (d) is carried out in two stages. Here, the reaction of the phosgene with the amine or amines is carried out at from 0 to 160° C., for example from 20 to 130° C., in a first stage which is also known as cold phosgenation, with a time of from about 0.5 min to 2 hours being allowed for the reaction between amine and phosgene. Subsequently, in a second stage also known as hot phosgenation, the temperature is increased over a period of generally from about 1 minute to 5 hours, for example from about 1 minute to 3 hours, to from 60 to 190° C., in particular from 70 to 170° C.

In a further embodiment of the invention, superatmospheric pressure, generally up to 100 bar or less, preferably from 1 bar to about 50 bar, particularly preferably from 2 bar to 25 bar, in particular from 3 bar to 12 bar, can be applied during the reaction (d). In a further embodiment of the invention, the reaction is carried out at about 1 bar (ambient pressure). In a further embodiment, a pressure below ambient pressure is employed.

In a step (e), the isocyanates formed are separated off and, if necessary, purified.

Excess phosgene can be removed at a temperature of from 50 to 180° C. after the reaction. The removal of the solvent is preferably carried out under reduced pressure, for example at a pressure of 500 mbar or less, preferably 100 mbar or less. In general, the various solvent components are separated off in the order of their boiling points, with mixtures of various components also being able to be separated off in a single process stage. The isocyanate obtained can subsequently be fractionated.

In a step (f), the hydrogen chloride is separated off and, if necessary, purified. In the reaction (d) of phosgene with amine, hydrogen chloride is usually obtained in gaseous form in admixture with phosgene and, typically, small amounts of further gases such as carbon monoxide, carbon dioxide, nitrogen and traces of solvents used in the preparation of isocyanate. Phosgene and high-boiling secondary constituents can also be separated off by distillation. A stream consisting essentially of hydrogen chloride is obtained. Traces of organic compounds such as phosgene and solvent residues present therein can be removed by absorption, adsorption, distillation or extraction in a downstream purification stage. To purify the hydrogen chloride stream, it is also possible for it to be absorbed in water or dilute hydrochloric acid and, after volatile constituents have been separated off, desorbed again in a further step. Solvent residues can also be removed from the hydrogen chloride stream by catalytic combustion. The hydrogen chloride stream, which may have been purified in this manner, is passed to catalytic hydrogen chloride oxidation.

In one embodiment of the process of the present invention, the stream comprising hydrogen chloride is purified by passing it over a purification bed so that solvent residues present in it are absorbed on the purification bed.

The purification bed comprises appropriate absorbents, preferably in the form of, for example, spheres, extrudates or pellets. Materials which are suitable as absorbents are, for example, activated carbon, aluminum oxide, titanium oxide, silicon dioxide, iron oxide, zeolites and molecular sieves. Suitable materials may also comprise metal oxides or metal halides, e.g. copper or ruthenium oxides or halides or mixtures thereof, on a support made of a refractory organic material such as aluminum oxide, titanium oxide or silicon dioxide. Preferred absorbents are aluminum oxide, activated carbon and clay minerals.

In a further embodiment of the process of the present invention, the purification of the stream comprising hydrogen chloride is carried out by catalytic combustion of the solvent residues present therein. For this purpose, oxygen or a gas stream comprising oxygen, for example air, oxygen-enriched air, technical-grade or pure oxygen, is mixed into the stream comprising hydrogen chloride and the resulting stream is passed over a fixed bed of oxidation catalyst. Suitable catalysts comprise, for example, aluminum oxide, magnesium oxide, iron oxide, titanium dioxide, zirconium dioxide or mixtures thereof. The catalytic combustion of the solvent residues (hydrocarbons and/or chlorinated hydrocarbons) over the abovementioned catalysts can effect partial conversion of the hydrogen chloride present into chlorine. This partial conversion can be, for example, up to 40%, preferably up to 20%, for example from about 5 to 20%.

The catalytic combustion as purification stage can also be regarded as the first stage of a two-stage catalytic hydrogen chloride oxidation, with the first stage over the abovementioned catalysts leading to partial conversion and the second stage as step (g) over the ruthenium-containing catalysts described below being carried out to full conversion, for example a conversion of at least 70%, based on the first and second stages. The first stage, which is carried out over inexpensive, relatively insensitive catalysts, effects oxidation of the solvent traces, which lead to carbon deposits, to carbon dioxide. In this way, the expensive ruthenium catalyst used in the second stage is protected against impurities which form carbon deposits.

In a step (g), the hydrogen chloride which has been separated off in step (f) is catalytically oxidized by means of oxygen to form chlorine.

For this purpose, the hydrogen chloride stream, which may have been purified and may be a recycled stream comprising hydrogen chloride, an oxygen-containing stream and, if desired, an oxygen-containing recycled stream are fed into an oxidation zone and hydrogen chloride is partly oxidized to chlorine in the presence of a catalyst, giving a product gas stream comprising chlorine, unreacted oxygen, unreacted hydrogen chloride and water vapor.

In the catalytic process, which is also known as the Deacon process, hydrogen chloride is oxidized by oxygen to form chlorine in an exothermic equilibrium reaction, with water vapor being obtained. Customary reaction temperatures are in the range from 150 to 500° C., and customary reaction pressures are in the range from 1 to 25 bar. Since the reaction is an equilibrium reaction, it is advantageous to use the lowest possible temperatures at which the catalyst still displays sufficient activity. It is also advantageous to use oxygen in superstoichiometric amounts. For example, a two- to four-fold oxygen excess is customary. Since no selectivity losses have to be feared, it may be economically advantageous to carry out the reaction at relatively high pressures and at residence times longer than those at atmospheric pressure.

Suitable catalysts comprise ruthenium oxide, ruthenium chloride or other ruthenium compounds on silicon dioxide, aluminum oxide, titanium dioxide or zirconium dioxide as support. Suitable catalysts can, for example, be obtained by application of ruthenium chloride to the support and subsequent drying or drying and calcination. Suitable catalysts can also comprise, in addition to or in place of a ruthenium compound, compounds of other noble metals, for example, gold, palladium, platinum, osmium, iridium, silver, copper or rhenium. Suitable catalysts may also comprise chromium (III) oxide.

Customary reaction apparatuses in which the catalytic hydrogen chloride oxidation is carried out are fixed-bed and fluidized-bed reactors. The oxidation of hydrogen chloride can be carried out in a plurality of stages.

The catalytic hydrogen chloride oxidation can be carried out adiabatically or preferably isothermally or approximately isothermally, batchwise or preferably continuously as a fluidized-bed or fixed-bed process, preferably as a fixed-bed process, particularly preferably in shell-and-tube reactors, over heterogeneous catalysts at reactor temperatures of from 180 to 500° C., preferably from 200 to 400° C., particularly preferably from 220 to 350° C., and a pressure of from 1 to 25 bar, preferably from 1.2 to 20 bar, particularly preferably from 1.5 to 17 bar and in particular from 2.0 to 15 bar.

In the case of isothermal or approximately isothermal operation, it is also possible to use a plurality, for example from 2 to 10, preferably from 2 to 6, particularly preferably from 2 to 5, in particular 2 or 3, reactors connected in series with additional intermediate cooling. It is possible for all of the oxygen to be fed in together with the hydrogen chloride upstream of the first reactor or for the introduction of the oxygen to be divided among the various reactors. This series arrangement of individual reactors can also be combined in one apparatus.

A preferred embodiment comprises using a structured catalyst bed in which the catalyst activity increases in the flow direction. Such structuring of the catalyst bed can be achieved by impregnating the catalyst support with different amounts of active composition or by differing dilution of the catalyst with an inert material.

Inert materials which can be used are, for example, rings, cylinders or spheres made of titanium dioxide, zirconium dioxide or mixtures thereof, aluminum oxide, steatite, ceramic, glass, graphite or stainless steel. In the case of the preferred use of shaped catalyst bodies, the inert material preferably has similar external dimensions.

Shaped catalyst bodies can be of any shape; preference is given to pellets, rings, cylinders, stars, wagon wheels or spheres and particular preference is given to rings, cylinders or star extrudates.

Suitable heterogeneous catalysts are, in particular, ruthenium compounds or copper compounds on support materials and may also be doped. Preference is given to doped or undoped ruthenium catalysts. Suitable support materials are, for example, silicon dioxide, graphite, titanium dioxide having a rutile or anatase structure, zirconium dioxide, aluminum oxide or mixtures thereof, preferably titanium dioxide, zirconium dioxide, aluminum oxide or mixtures thereof, particularly preferably γ- or δ-aluminum oxide or mixtures thereof.

The supported copper or ruthenium catalysts can be obtained, for example, by impregnating the support material with aqueous solutions of $CuCl_2$ or $RuCl_3$ and, if desired, a promoter for doping, preferably in the form of their chlorides. Shaping of the catalyst can be carried out after or preferably before impregnation of the support material.

Promoters suitable for doping are alkali metals such as lithium, sodium, potassium, rubidium and cesium, preferably lithium, sodium and potassium, particularly preferably potassium, alkaline earth metals such as magnesium, calcium, strontium and barium, preferably magnesium and calcium, particularly preferably magnesium, rare earth metals such as scandium, yttrium, lanthanum, cerium, praseodymium and neodymium, preferably scandium, yttrium, lanthanum and cerium, particularly preferably lanthanum and cerium, or mixtures thereof.

The shaped bodies can subsequently be dried and, if appropriate, calcined at from 100 to 400° C., preferably from 100 to 300° C., for example under a nitrogen, argon or air atmosphere. Preference is given to firstly drying the shaped bodies at from 100 to 150° C. and subsequently calcining them at from 200 to 400° C.

The conversion of hydrogen chloride in a single pass can be restricted to from 15 to 90%, preferably from 40 to 85%, particularly preferably from 50 to 70%. Unreacted hydrogen chloride can be separated off and partly or wholly recirculated to the catalytic hydrogen chloride oxidation. The volume ratio of hydrogen chloride to oxygen at the reactor inlet is generally from 1:1 to 20:1, preferably from 2:1 to 8:1, particularly preferably from 2:1 to 5:1.

Compared to the production of chlorine by electrolysis of hydrogen chloride, the catalytic hydrogen chloride oxidation has the advantages that no expensive electrical energy is required, that no hydrogen which may cause safety problems is obtained as coproduct and that the hydrogen chloride feed does not have to be completely pure.

The heat of reaction of the catalytic hydrogen chloride oxidation can be advantageously utilized for the generation of high-pressure steam. This can be used for operating the phosgenation reactor and the isocyanate distillation columns.

In a step (h), the chlorine formed is separated off. The separation step usually comprises a plurality of stages, namely the separation and, if desired, recirculation of unreacted hydrogen chloride from the product gas stream from the catalytic hydrogen chloride oxidation, drying of the resulting stream which consists essentially of chlorine and oxygen and separation of chlorine from the dried stream.

The separation of unreacted hydrogen chloride and water vapor formed from the product gas stream from the hydrogen chloride oxidation can be carried out by cooling so as to condense out aqueous hydrochloric acid. It is also possible for hydrogen chloride to be adsorbed in dilute hydrochloric acid or water.

In one embodiment of the invention, hydrogen chloride is separated off as described below. In an absorption stage, the product gas stream from the hydrogen chloride oxidation is brought into contact with dilute hydrochloric acid or water having a concentration c1 in an absorption zone and hydrogen chloride is absorbed in the dilute hydrochloric acid, giving a hydrochloric acid having a concentration c2 and a gas stream comprising chlorine and oxygen. In a desorption stage, the absorbed hydrogen chloride is liberated again from the hydrochloric acid having a concentration c2 in a desorption zone. The liberated hydrogen chloride can be recirculated at least partly, preferably wholly, as recycled stream comprising hydrogen chloride to the oxidation zone where further chlorine is recovered from the recirculated hydrogen chloride. A dilute hydrochloric acid having a concentration c1 can in this way be recovered as absorption medium and be recirculated to the absorption zone. Part of the dilute hydrochloric acid having a concentration c1 can also be discharged from the process. It is also possible, as described in EP-A 1 099 666, for part of the water to be separated off in a low-pressure column and the resulting more concentrated hydrochloric acid to be recirculated to the hydrogen chloride desorption zone.

Suitable absorption media are water and any dilute hydrochloric acid which is not saturated with hydrogen chloride. Its concentration c1 will usually be up to 30% by weight of hydrogen chloride, for example from about 15 to 20% by weight. The absorption temperature is usually from 0 to 150° C., preferably from 30 to 100° C., and the absorption pressure is usually from 0.5 to 20 bar, preferably from 1 to 10 bar. The desorption is preferably carried out in a desorption column. The desorption pressure is usually from 0.3 to 10 bar, preferably from 0.5 to 5 bar. The work-up of the product streams from the hydrogen chloride oxidation and the separation of hydrogen chloride can also be carried out as in EP-A 0 765 838.

The separation/work-up gives a gas stream which comprises chlorine and oxygen or consists essentially of these gases. It usually still contains traces of moisture. For this reason, it is usual to carry out a drying step in which the gas stream comprising chlorine and oxygen is freed of traces of moisture by bringing it into contact with suitable desiccants. Suitable desiccants are, for example, concentrated sulfuric acid, molecular sieves or hygroscopic adsorbents.

Finally, chlorine is separated off from the dried gas stream. This also produces an oxygen-containing stream which can be recirculated as recycled stream to the oxidation zone. The chlorine is preferably separated off by distillation, usually at from −20 to +50° C. and a pressure in the range from 1 to 20 bar in a distillation column having from 10 to 100 theoretical plates.

This leaves a stream which consists essentially of chlorine and is greatly depleted in bromine and iodine compared to the first partial amount of chlorine used or even no longer contains any significant amounts of bromine and iodine. At least part of this chlorine stream is recirculated as second partial amount of chlorine to step (c).

The invention is illustrated below with reference to the figures.

Each of the figures shows a block diagram of an embodiment of the process of the present invention.

A first substream of chlorine 34, containing less than 400 ppm of bromine and iodine, a second substream of chlorine 33 and a carbon monoxide stream 35 are fed into the phosgene synthesis stage 1 and are there reacted to form phosgene, with carbon monoxide preferably being used in excess. The resulting product gas stream 2, which consists essentially of phosgene and carbon monoxide and may additionally contain traces of chlorine, carbon tetrachloride and inerts such as nitrogen, is passed to the separation stage 3 and is there separated, preferably by condensation of phosgene or by distillation, into an offgas stream 4 which consists essentially of carbon monoxide and may contain traces of chlorine and a stream 5 comprising phosgene. The carbon monoxide stream 4 can also be recirculated to the phosgene synthesis. The phosgene stream 5 also contains the proportions of bromine and iodine present in the chlorine used. These can be present both in molecular form and in chemically bound form (e.g. as bromophosgene). This stream 5, a stream 6 comprising amine, a phosgene recycled stream 17 and a solvent recycled stream 10 are fed into the phosgenation stage 7 where the reaction of amine with phosgene to form isocyanate and hydrogen chloride takes place. The phosgenation stage 7 can be configured as, for example, a stirred vessel, a cascade of stirred vessels, a reaction column or a tube reactor with upstream mixing device or as a combination of the abovementioned apparatuses. The phosgenation can be carried out in two stages as a cold phosgenation with subsequent hot phosgenation. This gives a liquid product stream 8 comprising solvent, isocyanate and by-products (e.g. urea, oligomers) from which the solvent is separated off in the subsequent separation stage 9, preferably by distillation. The solvent stream 10 is, after replacement of solvent losses, recirculated to the phosgenation stage 7. The isocyanate stream 11 which remains is separated into desired product 13 and high boilers 14 in the purification stage 12. Oligomers obtained as high boilers may also be able to be regarded as desired product or product of value. Hydrogen chloride formed in the phosgenation reaction and excess phosgene leave the phosgenation stage 7 as gas stream 15 which may further comprise solvent residues, low-boiling by-products, carbon monoxide, carbon dioxide and inert gases (for example nitrogen, argon). Phosgene and solvent residues are separated off from this in the separation stage 16, preferably by distillation, and are recirculated as recycled stream 17 to the phosgenation stage 7. This leaves a hydrogen chloride stream 18 which may still contain traces of solvent, phosgene or inerts. This may, if desired, be freed of solvent traces in a purification stage 19, preferably by absorption. A purified hydrogen chloride stream 20 is obtained. This and an oxygen-containing stream 21, an oxygen-containing recycled stream 31 and a recycled stream 37 comprising hydrogen chloride are fed into a hydrogen chloride oxidation reactor 22 in which hydrogen chloride is oxidized catalytically to chlorine. As oxygen-containing stream, it is possible to use, for example, pure oxygen, 94% strength by volume oxygen from a pressure swing absorption (technical-grade oxygen) or oxygen-enriched air. This gives a product gas stream 23 which consists essentially of chlorine, unreacted oxygen, unreacted hydrogen chloride and water vapor. The product gas stream 23 is introduced into a phase contact apparatus 24 and there brought into contact with dilute hydrochloric acid 25. The stream 26 which is laden with the hydrogen chloride which has been separated off and consists of more highly concentrated hydrochloric acid is passed to the desorption column 36 in which the absorbed hydrogen chloride is liberated again and this is conveyed as recycled stream 37 to the hydrogen chloride oxidation reactor 22. The dilute hydrochloric acid recovered in the desorption is, if desired, cooled and partly recirculated as stream 38 to the phase contact apparatus 24. A stream 27 which has been largely freed of hydrogen chloride and comprises chlorine, oxygen and water vapor leaves the phase contact apparatus 24 and is passed to a drying stage 28. In the drying stage 28, the gas stream 27 is brought into contact with a suitable absorbent such as sulfuric acid, molecular sieves or further hygroscopic adsorbents such as silica gel or zeolites and is thus freed of traces of water. The dried gas stream 29 comprising chlorine and oxygen is passed to the separation stage 30 in which chlorine is separated off, preferably by condensation. This gives an oxygen-containing stream which may also contain, for example, up to 10% by volume of chlorine and this is recirculated as recycled stream 31 to the hydrogen chloride oxidation reactor. To avoid accumulation of inert gaseous constituents such as nitrogen, argon (possibly from the oxygen-containing stream 21 if pure oxygen has not been used) or carbon dioxide (from the phosgenation), provision is made for a purge stream 32. A stream 33 consisting essentially of chlorine is also obtained from the separation stage 30, and this is recirculated as second chlorine substream to the phosgene synthesis stage 1.

We claim:

1. A process for preparing organic isocyanates, which comprises
   (a) introducing a first partial amount of chlorine, wherein the first partial amount of chlorine has a content of free and bound bromine and iodine of at least 50 ppm and less than 400 ppm;
   (b) introducing a second partial amount of chlorine;
   (c) reacting the first and second partial amounts of chlorine with carbon monoxide to form phosgene;
   (d) reacting the phosgene with one or more primary amines to form an isocyanate and hydrogen chloride;
   (e) separating off and optionally purifying the isocyanate;
   (f) separating off and optionally purifying the hydrogen chloride;
   (g) catalytically oxidizing at least part of the hydrogen chloride separated off and optionally purified in step (e) with a gas comprising oxygen to form chlorine;
   (h) separating off the chlorine formed in step (g)
   wherein the second partial amount of chlorine in step (b) comprises at least a partial amount of the chlorine formed in step (g).

2. A process as claimed in claim 1, wherein the chlorine of the first partial amount of chlorine is obtained by electrolysis of a solution comprising chloride ions.

3. A process as claimed in claim 1, wherein the chlorine of the first partial amount is depleted in bromine and/or iodine in a purification stage.

4. A process as claimed in claim 1, wherein the second partial amount of chlorine in step (b) comprises essentially the total amount of the chlorine formed in step (g), and the first partial amount of chlorine in step (a) is introduced so that the sum of first and second partial amounts of chlorine remains constant.

5. A process as claimed in claim 1, wherein the second partial amount of chlorine comprises at least 70% of the sum of first and second partial amounts of chlorine.

6. A process as claimed in claim 1, wherein the chlorine of the first partial amount has a content of free and bound bromine and iodine of less than 100 ppm.

7. A process as claimed in claim 1, wherein the oxidizing step is carried out in the presence of a heterogeneous catalyst.

8. A process as claimed in claim 7, wherein said gas of the oxidizing step further comprises a catalyst comprising ruthenium oxide and said oxidizing step is carried out on a support selected from the group consisting of silicon dioxide, aluminum oxide, titanium dioxide, zirconium dioxide and mixtures thereof.

9. A process as claimed in claim 1, wherein the one or more primary are selected from the group consisting of the isomeric, monomeric and oligomeric diphenylmethanediamines, isomeric toluenediamines, isophoronediamine, hexamethylenediamine and mixtures thereof.

10. A process as claimed in claim 1, wherein the oxidizing step is carried out in a fixed-bed or fluidized-bed reactor.

* * * * *